(12) United States Patent
Namekata et al.

(10) Patent No.: US 8,940,931 B2
(45) Date of Patent: Jan. 27, 2015

(54) PRODUCTION METHOD FOR REFINED 6-BROMO-2-NAPHTHALENECARBOXYLIC ACID PRODUCT

(75) Inventors: Takeshi Namekata, Kashima (JP); Ikuo Ito, Kashima (JP)

(73) Assignee: Air Water Inc., Hokkaido (JP)

( * ) Notice: Subject to any disclaimer, the term of this patent is extended or adjusted under 35 U.S.C. 154(b) by 92 days.

(21) Appl. No.: 13/881,313

(22) PCT Filed: Oct. 28, 2010

(86) PCT No.: PCT/JP2010/069188
§ 371 (c)(1),
(2), (4) Date: Apr. 24, 2013

(87) PCT Pub. No.: WO2012/056544
PCT Pub. Date: May 3, 2012

(65) Prior Publication Data
US 2013/0225860 A1    Aug. 29, 2013

(51) Int. Cl.
*C07C 51/02* (2006.01)
*C07C 51/43* (2006.01)
*C07C 51/487* (2006.01)
*C07C 51/41* (2006.01)

(52) U.S. Cl.
CPC .............. *C07C 51/487* (2013.01); *C07C 51/02* (2013.01); *C07C 51/412* (2013.01); *C07C 51/43* (2013.01)
USPC .......................................... 562/511; 562/409

(58) Field of Classification Search
CPC ..... C07C 51/487; C07C 51/02; C07C 51/412; C07C 51/43
USPC .................................................. 562/409, 511
See application file for complete search history.

(56) References Cited

FOREIGN PATENT DOCUMENTS

| | | |
|---|---|---|
| CN | 101402560 A | 4/2009 |
| JP | 60-500815 A | 5/1985 |
| JP | 2-76837 A | 3/1990 |
| JP | 7-179407 A | 7/1995 |
| JP | 10-195018 A | 7/1998 |
| JP | 11-152265 A | 6/1999 |
| JP | 2004-091428 A | 3/2004 |
| JP | 2007-015952 A | 1/2007 |
| WO | 84/03505 A1 | 9/1984 |

OTHER PUBLICATIONS

Office Action in corresponding Chinese application No. 201080069839.0, dated Jun. 5, 2014 (4 pages).
International Search Report issued in PCT/JP2010/069188 mailed on Nov. 22, 2010 (4 pages).
Patent Abstracts of Japan for Publication No. 02-076837, Publication Date: Mar. 16, 1990 (1 Page).
Journal of Organic Chemistry, vol. 23, Apr. 1958, pp. 633-635 (3 pages).

*Primary Examiner* — Yevegeny Valenrod
(74) *Attorney, Agent, or Firm* — Osha Liang LLP

(57) ABSTRACT

The present invention provides a method, as a means for industrially producing a refined 6-bromo-2-naphthalenecarboxylic acid product from a crude 6-bromo-2-naphthalenecarboxylic acid product, comprising: causing the above crude product to react with sodium hydroxide in water to precipitate a sodium salt of 6-bromo-2-naphthalenecarboxylic acid; performing recrystallization treatment for the obtained precipitate; causing the obtained crystal to react with acid in water to precipitate 6-bromo-2-naphthalenecarboxylic acid; and recovering the obtained precipitate.

2 Claims, No Drawings

PRODUCTION METHOD FOR REFINED 6-BROMO-2-NAPHTHALENECARBOXYLIC ACID PRODUCT

TECHNICAL FIELD

The present invention relates to a method of refining a crude 6-bromo-2-naphthalenecarboxylic acid material (referred also to as "crude BNA product" in the present invention) to produce a refined 6-bromo-2-naphthalenecarboxylic acid (referred also to as "refined BNA product" in the present invention) which is refined to such an extent of being usable as raw materials for medicines and agrichemicals.

BACKGROUND ART

6-Bromo-2-naphthalenecarboxylic acid (referred also to as "BNA", hereinafter) is used as an intermediate raw material for medicines and agrichemicals. As medicines and agrichemicals are such that impurities are particularly undesirable to be mixed therein, highly-pure materials with reduced impurity concentration as much as possible are also required for the intermediate materials to be used for those purposes.

Patent Document 1 below discloses a production method for the above BNA, in which 6-bromo-2-methylnaphthalene is oxidized by molecular oxygen in a solvent under the presence of an oxidative catalyst thereby to produce BNA, wherein the solvent contains lower aliphatic carboxylic acid and the catalyst comprises a heavy-metal compound and a bromine compound.

However, when BNA is produced under the condition specifically described in the above literature, problems occur including that unignorable impurities remain and the refinement thereof is not easy.

More specifically, Patent Document 1 recommends, as a preferred condition for the oxidation reaction, to employ a reaction temperature of 120 to 200 degrees C. and a reaction pressure of 10 to 30 kg/cm$^2$ (0.98 to 2.94 MPa). A specific example employs a reaction condition of 175 degrees C. and 30 kg/cm$^2$. Such a reaction condition was considered to be indeed satisfactory with regard to the productivity, but the purity of BNA in the obtained product was poor. Accordingly, in order to provide a product with high purity of BNA, advanced refining treatment was necessary to be performed for the product obtained through the above method. In addition, another problem was the high cost for the necessity of facilities comprising special materials because of the above oxidation reaction being executed under a high pressure.

The present inventors searched for a means for solving the above problems. As a result, a method has been found out which produces relatively pure BNA with a high yield by modifying conditions for oxidation (Patent Document 2). As disclosed in Patent Document 2, the oxidation reaction for 6-bromo-2-methylnaphthalene is executed under a lower temperature and a lower pressure than those disclosed in Patent Document 1 thereby to allow for enhancing the purity of BNA in the product.

PATENT DOCUMENT

[Patent Document 1] Japanese Published Patent Application No. 10-195018
[Patent Document 2] Japanese Published Patent Application No. 2004-91428

SUMMARY OF THE INVENTION

Problems to be Solved by the Invention

In recent years, however, the purity required for a refined BNA product is particularly increasing, and a means for further increasing the purity is desired.

In view of such circumstances, an object of the present invention is to provide a means for industrially producing a refined BNA product from a crude BNA product.

Means for Solving the Problems

The present inventors proceeded with the study for solving the above problems. As a result, the knowledge has been obtained as below.

In general, aromatic carboxylic acid is easy to dissolve in alkaline aqueous solution. Actually, BNA easily dissolves in potassium hydroxide aqueous solution at ordinary temperatures. If, however, BNA is caused to react with sodium hydroxide in water, then the produced sodium salt of BNA (referred also to as "NaBNA", hereinafter) has a low solubility in water as the solvent. Accordingly, NaBNA remains in a solid state in the reaction liquid, so that this liquid does not easily become solution.

The present inventors have found out that this property of BNA can be utilized to perform recrystallization and refinement in the state of NaBNA thereby to effectively remove impurities. The present inventors have thus found out a means for easily producing a refined BNA product with particularly high purity in such a manner.

The present invention has been accomplished on the basis of the aforementioned knowledge. According to one aspect of the present invention, there is provided a production method for a refined 6-bromo-2-naphthalenecarboxylic acid product (refined BNA product), comprising: causing a crude 6-bromo-2-naphthalenecarboxylic acid product (crude BNA product) to react with sodium hydroxide in water to precipitate a sodium salt of 6-bromo-2-naphthalenecarboxylic acid (NaBNA); performing recrystallization treatment for the obtained precipitate; causing the obtained crystal to react with acid in water to precipitate 6-bromo-2-naphthalenecarboxylic acid (BNA); and recovering the obtained precipitate of BNA.

It is preferred herein that the reaction of the crude BNA product and sodium hydroxide in water is performed by causing the crude BNA product to react with sodium hydroxide aqueous solution.

Further, when the obtained crystal by the above recrystallization treatment is caused to react with acid in water to precipitate BNA, it is preferred to prepare aqueous solution dissolved therein with the above crystal and drop acid into this aqueous solution.

According to another aspect of the present invention, there is provided a production method for a refined 6-bromo-2-naphthalenecarboxylic acid product (refined BNA product), comprising: causing a crude 6-bromo-2-naphthalenecarboxylic acid product (crude BNA product) to react with potassium hydroxide in water to obtain an aqueous solution; acidifying the obtained aqueous solution to obtain a precipitate; causing the precipitate to react with sodium hydroxide in water to precipitate a sodium salt of 6-bromo-2-naphthalenecarboxylic acid (NaBNA); performing recrystallization treatment for the obtained precipitate; causing the obtained crystal to react with acid in water to precipitate 6-bromo-2-naphthalenecarboxylic acid (BNA); and recovering the obtained precipitate of BNA.

It is preferred herein that the reaction of the crude BNA product and potassium hydroxide in water is performed by causing the crude BNA product to react with potassium hydroxide aqueous solution. It is also preferred that the reaction of the above precipitate and sodium hydroxide in water is performed by causing the above precipitate to react with sodium hydroxide aqueous solution. Preferred embodiment where the obtained crystal by the above recrystallization treatment is caused to react with acid in water to precipitate BNA is as previously described.

Advantageous Effect of the Invention

According to the production method of the present invention, a refined BNA product with particularly high purity can be industrially produced from a crude BNA product.

BEST MODE FOR CARRYING OUT THE INVENTION

The production method for a refined BNA product according to the present invention will hereinafter be described in detail.

(1) Crude BNA Product

The production method for a crude BNA product is not limited. A method described in Patent Document 1 or 2 may be typically employed.

(2) Treatment Using Potassium Hydroxide

One embodiment according to the present invention comprises pretreatment in which aqueous solution obtained by causing a crude BNA product to react with potassium hydroxide in water is filtrated to remove extremely small amount of insoluble substances (which appear to be coloring substances, catalysts, and the like), and the obtained filtrated liquid is acidified to obtain a precipitate. Hereinafter, this treatment will be referred to as "KOH treatment", and the precipitate obtained by the KOH treatment as "KOH precipitate".

In the aqueous solution obtained by causing a crude BNA product to react with potassium hydroxide in water, BNA dissolves in a form of potassium ions and acid ions. Specific method for the reaction of the crude BNA product and potassium hydroxide in water may be freely selected. Respective solid substances of a crude BNA product and potassium hydroxide may be put into water to react. In view of stably performing the above reaction, it is preferred that a crude BNA product is dissolved in potassium hydroxide aqueous solution. In this case, the concentration and the amount of potassium hydroxide aqueous solution and the liquid temperature may be freely selected so long as capable of dissolving the crude BNA product. It is preferred that the concentration of potassium hydroxide aqueous solution is kept to the minimum necessary in consideration of increasing the productivity. Aqueous solution is typically used which includes 1.0 to 1.5 molar equivalent of potassium hydroxide relative to the crude BNA product as the raw material. In order to highly satisfy both the productivity and the quality (purity), it is preferred that the temperature where the crude BNA product is dissolved is about 15 to 35 degrees C.

The filtration of the aqueous solution obtained by the above reaction may be performed in accordance with known method in the art.

The filtrated liquid obtained by the above filtration, which includes the solution obtained by the above reaction, is acidified to obtain a precipitate. The precipitate obtained by this process includes BNA.

Detailed conditions for the acidification and other factors may be freely selected. Mineral acid, such as hydrochloric acid, sulfuric acid, nitric acid, and phosphoric acid, may be typically used, and the acidification is performed by dropping the mineral acid into the above filtrated liquid.

The precipitate obtained by this process, which contains BNA, is obtained as a residue after the filtration using known means in the art, and the residue is washed by water or other appropriate liquid to obtain a KOH precipitate.

In view of more effectively removing coloring substances and the like caused in the process for producing the crude BNA product, activated carbon may be added to the aqueous solution obtained by the above reaction in water of the crude BNA product and potassium hydroxide, and the liquid after the addition may be filtrated.

(3) Treatment Using Sodium Hydroxide

According to the method of the present invention, a crude BNA product or a KOH precipitate is caused to react with sodium hydroxide in water to precipitate NaBNA, the obtained precipitate is subjected to recrystallization treatment, the crystal obtained by this recrystallization treatment is caused to react with acid in water, and a precipitate is thus obtained which includes BNA with high purity.

When the crude BNA product or the KOH precipitate is caused to react with sodium hydroxide in water, NaBNA is produced. As this NaBNA has less solubility to water as the solvent than that of potassium salt of BNA, the above reaction produces a precipitate that include NaBNA if the solvent temperature is about room temperature.

Specific method for the reaction of the crude BNA product or the KOH precipitate and sodium hydroxide in water may be freely selected. Respective solid substances of a crude BNA product and sodium hydroxide may be put into water to react. In view of stably performing the above reaction, it is preferred that preliminarily prepared sodium hydroxide aqueous solution is caused to react with the crude BNA product or the KOH precipitate. In this case, the concentration and the amount of sodium hydroxide aqueous solution and the liquid temperature may be freely selected so long as capable of producing NaBNA from the crude BNA product or from the KOH precipitate. It is preferred that the concentration of sodium hydroxide aqueous solution is kept to the minimum necessary in consideration of increasing the productivity. Aqueous solution is typically used which includes 3.0 to 6.0 molar equivalent of sodium hydroxide relative to BNA contained in the crude BNA product or in the KOH precipitate.

Specific method for the recrystallization treatment to be performed to the obtained product including NaBNA may be freely selected. In order to highly satisfy both the productivity and the quality (purity), it is preferred that the crude BNA product or the KOH precipitate and sodium hydroxide aqueous solution are reacted to obtain liquid (reaction liquid) without being removed therefrom NaBNA, and the reaction liquid is heated to about 70 to 100 degrees C. to cause NaBNA to dissolve into the reaction liquid. The recrystallization treatment can be performed by a known approach in the art, such as by cooling the reaction liquid dissolved therein with NaBNA to about room temperature or by concentrating the reaction liquid.

The crystal obtained by this recrystallization treatment is subjected to filtration by known means in the art to remain as a residue, and the residue is washed.

This residue after the washing, which includes the crystal obtained by the above recrystallization treatment, is caused to react with acid in water, and NaBNA included in the residue is thereby to be BNA and a precipitate is thus obtained which includes BNA with high purity. Conditions for this reaction may be freely selected so long as capable of obtaining the above precipitate. The residue may be mixed with acidic liquid, or liquid dispersed therein with the residue may also be mixed with acidic liquid. In view of stably performing this process, it is preferred that the residue including NaBNA is dissolved into a small amount of water by heating them to obtain aqueous solution, and mineral acid, such as hydrochloric acid, sulfuric acid, nitric acid, and phosphoric acid, is dropped into the aqueous solution.

The precipitate obtained in such a manner is recovered, and more specifically, is subjected to filtration by known means in the art to remain as a residue, and the obtained residue is washed and then dried thereby to provide a refined BNA product.

EXAMPLES

The present invention will hereinafter be described more in detail with reference to examples, but the present invention is not limited to these examples.

High-performance liquid chromatography (HPLC) was used for analysis under the conditions below. Note that, in the examples, the BNA concentration (purity) in the refined BNA product is represented by a ratio (area %) based on the BNA peak area in the HPLC chart, and the yield of the refined BNA product relative to the crude BNA product is in terms of mol %.

Measurement Conditions
Column: Inertsil ODS-2
Length 250 mm, inner diameter 4.6 mm (available from GL Sciences Inc.)
Mobile phase: Methanol/0.1% phosphoric acid water, 1 ml/minute
(gradient where the mixing volume ratio is started from 7:3 and changed to 9:1 at 25 minutes elapsed, which is maintained until 40 minutes from the start)
Detector: UV (254 nm)

Example 1

A glass container of 500 ml, provided with a reflux condenser, a gas injecting tube, an exhaust tube, a temperature measurement tube, and an electromagnetic stirrer, was set up with 210 g (3.5 mol) of acetic acid, 1.66 g (6.66 mmol) of cobalt acetate tetrahydrate, 1.65 g (6.73 mmol) of manganese acetate tetrahydrate, 1.06 g (8.91 mmol) of potassium bromide, 10.0 g (45.2 mmol) of 6-bromo-2-methylnaphthalene, and 5.2 g (51.0 mmol) of acetic acid anhydride. An oxidation reaction for producing BNA was performed by stirring the mixture in the glass container during 4.5 hours under ordinary pressure while keeping the inner temperature of the glass container at 110 degrees C. and injecting pure oxygen with a flow rate of 0.2 litters/minute into the glass container.

After completing the reaction and cooling the reaction liquid to 30 degrees C., the cooled liquid was filtrated to obtain a precipitate as a residue. The obtained residue was dried under reduced pressure of 5 mmHg and 40 degrees C. until being of constant mass. A crude BNA product was thus obtained with a purity of 99.2% and a weight of 8.29 g.

A glass container of 200 ml, provided with a reflux condenser, a temperature measurement tube, and an electromagnetic stirrer and nitrogen atmosphere therein, was set up with 8.20 g of the above crude BNA product. In addition, 97 g of 6% sodium hydroxide aqueous solution was put into the glass container and the temperature was increased to 90 degrees C. so that BNA was dissolved to be converted to NaBNA, and they were then cooled to 25 degrees C. to obtain a precipitate of NaBNA. The obtained precipitate was subjected to filtration and a residue was recovered.

Subsequently, the residue was put into a glass container of 200 ml provided with a temperature measurement tube and an electromagnetic stirrer and nitrogen atmosphere therein. In addition, 97 g of water was put into the glass container and the temperature therein was raised to 50 degrees C. to dissolve the residue. A weight of 5.4 g of 36% hydrochloric acid was dropped into the aqueous solution in the glass container, and after the completion of the drop, the aqueous solution was held at 50 degrees C. during one hour. The temperature in the glass container was then decreased to 25 degrees C. to obtain a precipitate. The obtained precipitate was subjected to filtration to be recovered as a residue, and the residue was washed by 110 g of water. The residue after the washing was dried under reduced pressure of 5 mmHg and 40 degrees C. until being of constant mass.

A yellowish-white refined BNA product was thus obtained with a purity of 99.9% and a weight of 7.78 g. The yield of the refined BNA product was 95.5% relative to the crude BNA product.

Example 2

A glass container of 500 ml, provided with a reflux condenser, a gas injecting tube, an exhaust tube, a temperature measurement tube, and an electromagnetic stirrer, was set up with 210 g (3.5 mol) of acetic acid, 1.66 g (6.66 mmol) of cobalt acetate tetrahydrate, 1.65 g (6.73 mmol) of manganese acetate tetrahydrate, 1.06 g (8.91 mmol) of potassium bromide, 10.0 g (45.2 mmol) of 6-bromo-2-methylnaphthalene, and 5.2 g (51.0 mmol) of acetic acid anhydride. An oxidation reaction for producing BNA was performed by stirring the mixture in the glass container during 4.5 hours under ordinary pressure while keeping the inner temperature of the glass container at 110 degrees C. and injecting pure oxygen with a flow rate of 0.2 litters/minute.

After completing the reaction and cooling the reaction liquid to 30 degrees C., the cooled liquid was filtrated to obtain a precipitate as a residue. The obtained residue was dried under reduced pressure of 5 mmHg and 40 degrees C. until being of constant mass. A crude BNA product was thus obtained with a purity of 99.2% and a weight of 8.30 g.

A glass container of 100 ml, provided with a reflux condenser, a temperature measurement tube, and an electromagnetic stirrer, was set up with 8.20 g of the above crude BNA product along with 47.5 g of 5% potassium hydroxide aqueous solution, and they were stirred during 0.5 hours at 25 degrees C. The reaction liquid after the stirring was filtrated to remove an extremely small amount of insoluble substances, and 20 g of 36% hydrochloric acid was dropped into the filtrated liquid to produce a precipitate therein. The obtained precipitate was subjected to filtration and a residue was recovered.

The residue was then put into a glass container of 200 ml provided with a reflux condenser, a temperature measurement tube, and an electromagnetic stirrer and nitrogen atmosphere therein. In addition, 97 g of 6% sodium hydroxide aqueous solution was put into the glass container and the temperature was raised to 70 degrees C. so that BNA was dissolved to be converted to NaBNA, and they were then cooled to 25 degrees C. to obtain a precipitate. The obtained precipitate was subjected to filtration and a residue was recovered.

The residue obtained in such a manner was put into another glass container of 200 ml provided with a temperature measurement tube and an electromagnetic stirrer and nitrogen atmosphere therein. In addition, 97 g of water was added to the glass container and the temperature therein was raised to 50 degrees C. to dissolve the residue. A weight of 5.7 g of hydrochloric acid was dropped into the aqueous solution in the glass container, and after the completion of the drop, the aqueous solution was held at 50 degrees C. during one hour. The temperature in the glass container was then decreased to 25 degrees C. to obtain a precipitate. The obtained precipitate was subjected to filtration to be recovered as a residue, and the residue was washed by 110 g of water. The residue after the washing was dried under reduced pressure of 5 mmHg and 40 degrees C. until being of constant mass.

A white refined BNA product was thus obtained with a purity of 99.9% and a weight of 7.74 g. The yield of the refined BNA product was 95.1% relative to the crude BNA product.

Example 3

An autoclave, provided with a reflux condenser, a gas injecting tube, an exhaust tube, a temperature measurement tube, and an electromagnetic stirrer, was set up with 210 g (3.5 mol) of acetic acid, 3.34 g (13.4 mmol) of cobalt acetate tetrahydrate, 3.30 g (13.5 mmol) of manganese acetate tetrahydrate, 2.12 g (17.8 mmol) of potassium bromide, and 20.0 g (90.4 mmol) of 6-bromo-2-methylnaphthalene. An oxidation reaction for producing BNA was performed by stirring the mixture in the autoclave during 30 minutes while keeping the inner temperature of the autoclave at 150 degrees C. and injecting compressed air with a flow rate of 1.0 litter/minute to increase the inner pressure in the autoclave to 2.94 MPa.

After completing the reaction and cooling the reaction liquid to 30 degrees C., the cooled liquid was filtrated to obtain a precipitate as a residue, and the obtained residue was dried. A crude BNA product was thus obtained with a purity of 97.6% and a weight of 20.1 g.

Subsequently, a glass container of 200 ml, provided with a reflux condenser, a temperature measurement tube, and an electromagnetic stirrer and nitrogen atmosphere therein, was set up with 10.6 g (41.2 mmol) of the obtained crude BNA product by the above oxidation reaction, the purity thereof being 97.6%, along with 60.7 g of 5% potassium hydroxide aqueous solution, and they were stirred during 0.5 hours while keeping the inner temperature in the glass container at 25 degrees C. The reaction liquid after the stirring was filtrated to remove an extremely small amount of insoluble substances, and 24.0 g of 36% hydrochloric acid was dropped into the filtrated liquid to produce a precipitate therein. The obtained precipitate was subjected to filtration and a residue was recovered.

Thereafter, the residue was put into another glass container of 200 ml provided with a reflux condenser, a temperature measurement tube, and an electromagnetic stirrer and nitrogen atmosphere therein. In addition, 124 g of 6% sodium hydroxide aqueous solution was put into the glass container and the temperature was raised to 70 degrees C. so that BNA was dissolved to be converted to NaBNA, and they were then cooled to 25 degrees C. to obtain a precipitate. The obtained precipitate was subjected to filtration and a residue was recovered.

The residue obtained in such a manner was put into yet another glass container of 200 ml provided with a temperature measurement tube and an electromagnetic stirrer and nitrogen atmosphere therein. In addition, 125 g of water was added to the glass container and the temperature therein was raised to 50 degrees C. to dissolve the residue. The aqueous solution in the glass container was added thereto with 6.3 g of 36% hydrochloric acid and thereafter held at 50 degrees C. during one hour. The temperature in the glass container was then decreased to 25 degrees C. to obtain a precipitate. The obtained precipitate was subjected to filtration to be recovered as a residue, and the residue was washed by 140 g of water. The residue after the washing was dried under reduced pressure of 5 mmHg and 40 degrees C. until being of constant mass.

A white refined BNA product was thus obtained with a purity of 99.9% and a weight of 6.8 g. The yield of the refined BNA product was 65.7% relative to the crude BNA product.

Comparative Example 1

A glass container of 500 ml, provided with a reflux condenser, a gas injecting tube, an exhaust tube, a temperature measurement tube, and an electromagnetic stirrer, was set up with 210 g (3.5 mol) of acetic acid, 1.66 g (6.66 mmol) of cobalt acetate tetrahydrate, 1.65 g (6.73 mmol) of manganese acetate tetrahydrate, 1.06 g (8.91 mmol) of potassium bromide, 10.0 g (45.2 mmol) of 6-bromo-2-methylnaphthalene, and 5.2 g (51.0 mmol) of acetic acid anhydride. An oxidation reaction for producing BNA was performed by stirring the mixture in the glass container during 8 hours under ordinary pressure while keeping the inner temperature of the glass container at 110 degrees C. and injecting pure oxygen with a flow rate of 0.5 litters/minute.

After completing the reaction and cooling the reaction liquid to 30 degrees C., the cooled liquid was filtrated to obtain a precipitate as a residue. The obtained residue was dried under reduced pressure of 5 mmHg and 40 degrees C. until being of constant mass. A crude BNA product was thus obtained with a purity of 99.1% and a weight of 9.1 g.

A glass container of 100 ml, provided with a reflux condenser, a temperature measurement tube, and an electromagnetic stirrer, was set up with 8.20 g of the above crude BNA product along with 47.5 g of 5% potassium hydroxide aqueous solution, and they were stirred during 0.5 hours at 25 degrees C. The reaction liquid after the stirring was filtrated to remove an extremely small amount of insoluble substances, and 20.0 g of 36% hydrochloric acid was dropped into the filtrated liquid to produce a precipitate therein. The obtained precipitate was subjected to filtration and a residue was recovered.

As a result of analyzing the residue after being dried, the purity of BNA was 99.1%, which was not different from the purity of the above crude BNA product.

Comparative Example 2

A glass container of 100 ml, provided with a reflux condenser, a temperature measurement tube, and an electromagnetic stirrer, was set up with 5.0 g of the crude BNA product, obtained in Example 2, along with 29.0 g of 5% potassium hydroxide aqueous solution, and they were stirred during 0.5 hours at 25 degrees C. The reaction liquid after the stirring was filtrated to remove an extremely small amount of insoluble substances, and 13.0 g of 36% hydrochloric acid was dropped into the filtrated liquid to produce a precipitate therein. The obtained precipitate was subjected to filtration and a residue was recovered.

As a result of analyzing the residue after being dried, the purity of BNA was 97.6%, and the purity was not able to be enhanced.

The invention claimed is:
1. A production method for a refined 6-bromo-2-naphthalenecarboxylic acid product, comprising:

causing a crude 6-bromo-2-naphthalenecarboxylic acid product to react with sodium hydroxide in water to precipitate a sodium salt of 6-bromo-2-naphthalenecarboxylic acid;

performing recrystallization treatment for the obtained precipitate;

causing the obtained crystal to react with acid in water to precipitate 6-bromo-2-naphthalenecarboxylic acid; and recovering the obtained precipitate.

2. A production method for a refined 6-bromo-2-naphthalenecarboxylic acid product, comprising:

causing a crude 6-bromo-2-naphthalenecarboxylic acid product to react with potassium hydroxide in water to obtain an aqueous solution;

acidifying the obtained aqueous solution to obtain a precipitate;

causing the precipitate to react with sodium hydroxide in water to precipitate a sodium salt of 6-bromo-2-naphthalenecarboxylic acid;

performing recrystallization treatment for the obtained precipitate;

causing the obtained crystal to react with acid in water to precipitate 6-bromo-2-naphthalenecarboxylic acid; and recovering the obtained precipitate.

* * * * *